United States Patent [19]

Hupp et al.

[11] 4,104,318

[45] Aug. 1, 1978

[54] PROCESS FOR REMOVING ORGANIC OXYGEN-CONTAINING IMPURITIES FROM AN ORGANIC COMPOSITION IN THE PRESENCE OF STEAM

[75] Inventors: Stephen S. Hupp, Reserve Township, Allegheny County; Edward T. Sabourin, Allison Park; Harold E. Swift, Gibsonia; Roger F. Vogel, Butler, all of Pa.

[73] Assignee: Gulf Research & Development Company, Pittsburgh, Pa.

[21] Appl. No.: 801,038

[22] Filed: May 27, 1977

[51] Int. Cl.$^2$ ............................................. C07C 15/00
[52] U.S. Cl. ............................ 260/669 A; 260/669 R; 260/674 R
[58] Field of Search ............ 260/669 A, 669 R, 674 R

[56] References Cited

U.S. PATENT DOCUMENTS

| | | | |
|---|---|---|---|
| Re. 28,137 | 8/1974 | Turner et al. ................... | 260/669 R |
| 3,476,747 | 11/1969 | Hargis et al. ................... | 260/669 R |
| 3,557,238 | 1/1971 | Cunningham .................... | 260/680 E |
| 3,703,593 | 11/1972 | Turley et al. ................... | 260/669 R |
| 3,963,793 | 6/1976 | Weterings ....................... | 260/668 D |
| 3,965,206 | 6/1976 | Montgomery et al. ......... | 260/668 D |
| 3,998,902 | 12/1976 | Foster et al. .................... | 260/669 A |
| 4,044,067 | 8/1977 | Besozzi et al. .................. | 260/669 A |

*Primary Examiner*—Delbert E. Gantz
*Assistant Examiner*—Joseph A. Boska

[57] ABSTRACT

The amount of oxygen-containing impurities in an organic composition is reduced at an elevated temperature in the presence of steam using a catalyst comprising a Group VIb or Group VIII metal oxide or phosphate. For example, the amount of oxygen-containing organic impurities in a crude stilbene product obtained by the oxidative dehydrocoupling of toluene is catalytically reduced at high temperatures in the presence of steam and an iron oxide catalyst and the resulting stilbene product is reacted with ethylene to form styrene.

23 Claims, No Drawings

PROCESS FOR REMOVING ORGANIC OXYGEN-CONTAINING IMPURITIES FROM AN ORGANIC COMPOSITION IN THE PRESENCE OF STEAM

FIELD OF THE INVENTION

This invention relates to the catalytic reduction of oxygen-containing impurities in an organic composition. More particularly, the invention relates to the process for preparing styrene and its derivatives from toluene and its derivatives and to the purification of the intermediate stilbene and its derivatives. In this process toluene or a derivative of toluene is oxidatively dehydrocoupled using a solid oxidant to form a reaction product containing stilbene or a derivative of stilbene and this reaction product is reacted with ethylene over a disproportionation catalyst to form styrene or a derivative of styrene. Since water and any oxygenated organic compounds produced as by-products in the dehydrocoupling reaction will poison the disproportionation catalyst, these compounds are substantially eliminated before the ethenolysis reaction.

DESCRIPTION OF THE PRIOR ART

*Catalysis Reviews*, 3(1), 44(1969) discloses that polar compounds in feed streams to disproportionation catalysts will deactivate the catalysts. Specifically mentioned are water, acetone and methanol.

In U.S. Pat. No. 3,965,206 toluene is converted to styrene in a multi-stage procedure including the oxidative dehydrocoupling of toluene and terminating with the reaction of stilbene and ethylene by olefin metathesis. In this process a stilbene fraction containing some of the polar impurities present in the toluene dehydrocoupling effluent is separated from this reaction mixture. Polar impurities are removed from this stilbene fraction by one of the following specified techniques: by passage through a bed of absorbent material, by fractional crystallization, by solvent extraction, or by reaction in the absence of water with an active metal compound such as sodium metal or disodium stilbene.

SUMMARY OF THE INVENTION

When toluene is oxidatively dehydrocoupled at an elevated temperature with a solid oxidant, the crude reaction product includes unreacted toluene, benzene, bibenzyl, stilbene, water, carbon dioxide and trace amounts of organic oxygenated compounds in which the oxygen is present predominantly as carbonyl and hydroxyl. We have surprisingly discovered that this hot, crude reaction product can be directly treated at an elevated temperature for removal of the organic oxygenated compounds in the presence of the significant amount of steam that is present in the gaseous dehydrocoupling product stream without requiring an intermediate fractionation or water removal step and without requiring any type of intermediate cooling-reheating cycle. We have further discovered as an additional benefit of our invention that our procedure for directly treating this crude reaction product also converts a substantial portion of the undesired by-product bibenzyl into desired stilbene. In accordance with our invention this hot, gaseous, crude dehydrocoupling reaction product is directly treated over a catalyst containing one or more Group VIb or Group VIII metal oxides.

The dehydrocoupling of toluene is an oxidative reaction in which the oxygen is supplied by a suitable solid oxidant, such a metal oxide, a non-metal oxide or a mixture of these solid oxides. U.S. Pat. No. 3,476,747 discloses arsenic pentoxide, antimony, tetroxide and pentoxide, bismuth trioxide and manganese arsenate as the oxidant for the oxidative dehydrocoupling reaction. U.S. Pat. No. 3,494,956 discloses lead oxide, cadmium oxide and thallium oxide as the oxidant while U.S. Pat. No. 3,965,206 specifies lead oxide, cadmium oxide and bismuth oxide as the oxidant. Any suitable metal oxide, non-metal oxide or mixed oxides which can supply oxygen at the elevated temperatures for the oxidative reaction can be used in preparing the crude, stilbene-containing reaction product. The solid oxide oxidant is preferably supported on a suitable support such as fused silica, alumina, a silica alumina, and the like, or less preferably it can be unsupported.

The oxidative dehydrocoupling reaction is carried out at an elevated temperature, suitably between about 500° and about 700° C., preferably between about 550° and about 625° C. In carrying out the reaction, heated reactant such as toluene is introduced into the reactor preferably together with steam. Although some water is produced by the oxidative reactions taking place in the reactor, it is preferred that a substantial amount of water be added to the reactor in the form of steam to serve as a diluent and to help control the reaction. It is also possible to add molecular oxygen to supplement the oxygen provided by the solid oxidant, but it is preferred to carry out the reaction without using free oxygen. Molecular oxygen can be used in a mol ratio of molecular oxygen to toluene of zero to about 4, preferably zero to about 1.

The product stream from this oxidative dehydrocoupling stage includes water as steam and trace amounts of oxygen-containing organic compounds in addition to the hydrocarbon components. The amount of water present can range from about two to about 90 weight percent, more generally between about ten and about 75 weight percent, depending on the amount of water, added as steam to the dehydrocoupling reactor and the extent of the oxidative reactions taking place in this reactor. The oxygen-containing impurities are primarily aromatic compounds in which the oxygen is present as carbonyl and hydroxyl, with carbonyl predominating. These organic polar compounds will decompose in the presence of the disproportionation catalyst during the matathesis reaction producing in part, water. Since water causes the rapid deactivation of disproportionation catalysts, not only the water, but also the oxygen-containing organic compounds must be substantially eliminated from the feed stream to the ethenolysis reaction.

A significant and surprising advantage of the present process is that the hot, gaseous stream from the oxidative dehydrocoupling reactor can be directly contacted with a suitable catalyst, notwithstanding the presence of a large amount of steam, in order to substantially decompose the oxygen-containing organic compounds and thereby substantially reduce the concentration of these compounds. It is surprising that the catalyst is highly effective in decomposing the oxygen-containing compounds in the presence of a high steam concentration, since it was thought that the steam could have a substantial inhibiting effect on this decomposition. Another advantage of our process is that this catalyst which is effective in a high concentration of steam will additionally convert a substantial quantity of the by-product bibenzyl to stilbene.

The catalysts which are used in our purification procedure are Group VIb or Group VIII metal oxides or metal phosphates and mixtures of these. A special characteristic of these catalysts is that they will function in the presence of large quantities of steam at elevated temperatures without adverse effects. The group VIb metal oxides which are useful in this purification procedure are chromium oxide, molybdenum oxide and tungsten oxide. Group VIII metal oxides include iron oxide, cobalt oxide and nickel oxide. Noble metal oxides can also be used. Iron oxide is the preferred catalyst.

These catalysts can be compounded with one or more active components such as an alkali metal or alkaline earth metal compound, preferably a compound of potassium, which functions as a catalyst promoter by preventing excess carbon deposition on the catalyst and thereby promoting the life of the catalyst. Other metal oxides can also be used as promoters such as zinc oxide, copper oxide, small amounts of one or more additional members of the catalytic metal oxides such as chromium oxide used with iron oxide, and the like. These catalytic materials can be supported on a suitable inert carrier such as alumina, silica, silica-alumina, zirconia, and the like. They can also be admixed with one or more of these inert materials which then function as an inert diluent, or they can be used alone. The supported catalysts will desirably contain from 5 to about 50 weight percent of the Group VIb or Group VIII metal compound and preferably from about 10 to about 30 weight percent. The catalysts preferably are of a uniformly sized particulate form ranging from about one to 10 mm. in size, preferably sized intermediate in this range for convenient use in our process.

Examples of useful catalytic compositions include unsupported iron oxide promoted with minor amounts of chromium oxide and potassium, determined as potassium oxide or potassium carbonate. Another composition utilizes these components and a minor amount of molybdenum oxide as a further promoter. These compositions will contain at least about 35 percent and preferably between about 45 and 95 percent of the catalyst metal, from about 0.5 to about 50 percent, preferably about 5 to about 35 percent of one or more alkali and alkaline earth metal promoters, and about zero to about 20 percent, preferably about 5 to about 15 percent, of one or more additional promoters such as zinc oxide, chromium oxide, copper oxide, and the like. Chromia on alumina is another useful catalyst. Also useful is a nickel-calcium phosphate catalyst which is stabilized with a minor amount of chromium oxide. The surface area of these catalysts will generally range from about 0.5 to about 100 $M^2/g$.

The Group VIb and the Group VIII metal oxide or metal phosphate catalyst effects a significant reduction in the amount of the oxygen-containing organic compounds when used in the purification of the crude dehydrocoupling effluent. The amount of the oxygen-containing organic impurities is determined by analyzing for carbonyl content. It is believed that using the carbonyl content as the indicator of the presence of oxygen-containing organic impurities and as a measure of the degree of purification is reliable both because carbonyl in the form of aromatic aldehydes and ketones is considered to be the primary organic oxygen-containing impurity and for the further reason that this primary carbonyl impurity is believed to occur in a generally constant proportion with respect to the other organic, oxygen-containing impurities. We have found that it is desirable to reduce the amount of oxygen-containing compound in this purification step down to 50 parts per million (ppm) or less measured as carbonyl, preferably down to 35 ppm. or less carbonyl and most preferably down to 20 ppm. or less carbonyl, as determined by the following test for measuring trace carbonyl content.

A 0.8 to 5.0 g. sample of the dehydrocoupling effluent (the amount inversely adjusted to the anticipated concentration of carbonyl) is placed in the first of two 25 ml. flasks and 1.0 ml. of a saturated solution of 2,4-dinitrophenylhydrazine (100 ml. of water and 2.0 ml. of hydrochloric acid (sp. gr. 1.19) saturated with 2,4-dinitrophenylhydrazine) is added to both flasks. One drop of hydrochloric acid (sp. gr. 1.19) is added to both flasks with swirling. The flasks are heated at 55° C. in a water bath for 30 minutes with swirling every five minutes. The flasks are removed from the bath and allowed to stand at room temperature (25° C.) for 30 minutes with swirling every five minutes. Five ml. of alcohol potassium hydroxide solution (60 g. KOH/l. of methanol/water solution containing 11.2 percent water) is added to each flask with swirling and allowed to stand for five minutes. Following this each flask is diluted to volume with absolute methanol and mixed. Within 10 minutes of the addition of the alcoholic potassium hydroxide solution a portion of the wine-red colored solution containing the sample is placed in a cuvette and measured for absorbance at 430 m$\mu$ against the prepared blank (second flask). The concentration of carbonyl is determined from a calibration chart prepared from similar solutions containing a known amount of carbonyl and analyzed by the above technique.

Our purification procedure can suitably be carried out at a temperature between about 400° and about 700° C., preferably at a temperature between about 500° and about 600° C. and most preferably at the temperature of the dehydrocoupling effluent stream or somewhat lower. Thus, if the dehydrocoupling reactor is operating at 600° C., a convenient temperature in the purification reactor, taking into account inherent heat losses, will be about 525° to 575° C. Pressure is not a critical factor in the purification reactor and most generally will be atmospheric or slightly higher. The crude product stream is passed over the catalyst at a liquid hourly space velocity, LHSV, of between about 0.1 and about 50, preferably between about 0.5 and about 10 for most effective removal of the oxygenated organic impurity.

The product leaving the purification reactor contains toluene, benzene, stilbene, water, carbon dioxide, a residual amount of bibenzyl, and desirably no more than that residual amount of the undesired oxygen-containing organic compound which can be tolerated by the disproportionation catalyst. Since the water in this effluent stream from the purification stage will deactivate the disproportionation catalyst, it is removed prior to the methathesis reactor. Any conventional means for removing water such as by condensation, selective absorption by molecular sieves, azeotroping, and the like can suitably be used. Water is removed from the stream going to the metathesis reaction to an amount of 20 or less ppm., preferably to an amount of 10 or less ppm. The carbon dioxide is also removed following the purification stage.

This product stream from the oxidative dehydrocoupling reaction, with both the water and the oxygenated organic compounds being substantially removed, is in condition for the ethenolysis reaction. The ethylene can be added to this purified product stream prior to its introduction into the reactor or the ethylene can be added directly to the metathesis reactor. Although one mol of ethylene will react by metathesis with one mol of stilbene to form two mols of styrene, it is preferred that an excess of ethylene be used to help drive the reaction to completion. Therefore, a mol ratio of ethylene to stilbene of between about 1:1 to about 100:1 can suitably be used, but it is preferred that a mol ratio of about 2:1 to about 20:1 be used.

In this olefin metathesis reaction between the stilbene and the ethylene, an olefin disporportionation catalyst is used. Examples of suitable catalysts include the oxides of tungsten, molybdenum, rhenium, uranium, vanadium, niobium and tantalum and the sulfides and carbonyls of tungsten and molybdenum. These catalysts are carried on a suitable support such as alumina, silica, silica-alumina, a spinel such as zinc aluminate and magnesium aluminate, alumina-aluminum phosphate, and the like. The disproportionation catalyst can desirably be modified by the addition of a suitable compound of an alkali metal, alkaline earth metal, copper, silver, cobalt, nickel, and the like to control surface acidity.

The conditions for metathesis depend, in part, on the specific catalyst which is used. These conditions are well known in the art. The temperature for the metathesis reaction is generally within the range of about 150° to about 650° C., preferably it is between about 450° to about 650° C. The optimum temperature range has been determined to be between about 500° and about 600° C. The pressure in the reactor will generally be about atmospheric pressure for enhanced selectivity. The metathesis reaction is preferably carried out under conditions for maximum stilbene conversion. The term stilbene as used herein refers to trans-stilbene and/or cis-stilbene.

The metathesis reaction product stream will contain toluene, styrene, benzene, ethylene, and minor amounts of bibenzyl, stilbene and impurities. This stream is fractionated to recover the ethylene and toluene for recycle and to recover styrene and benzene as product. Bibenzyl can also be recovered and recycled to the oxidative dehydrocoupling reactor. If the bibenzyl is present in insignificant amounts or if it is not wanted, it can be discarded with the minor condensable impurities.

Although the above procedure as described provides for the purification of the total product stream from the oxidative dehydrocoupling reactor and use of this stream in the metathesis reaction, this procedure is not critical. Thus, the crude stream from the dehydrocoupling reactor can be fractionated and the recovered stilbene-containing fraction, preferably also containing bibenzyl, can then be treated in accordance with the purification procedure of the present invention.

In carrying out the purification procedure described herein, it may be desirable to add a small amount of free hydrogen to the purification reactor to enhance the removal of carbonyl and hydroxyl contamination. Such added hydrogen can comprise up to about 3 volume percent of the feed stream to the purification reactor to accomplish a suitable reduction in analyzed carbonyl content.

DESCRIPTION OF PREFERRED EMBODIMENTS

In the following examples, the dehydrocoupled product used as the feed to the purification reactor was the organic fraction which had been obtained by dehydrocoupling toluene over bismuth oxide or lead oxide and which had been collected and stored for later use. In carrying out the purification procedure, steam was introduced into the purification reactor in an amount similar to that which had been present in the crude dehydrocoupling product stream, that is, an equal volume ratio of water to the organic feed. The purification reactor was a tubular reactor about one inch I.D. (25.4 mm.) and about 18 inches (46 cm.) long. In all cases 20 ml. of catalyst was centered in the tube reactor with a layer of 10–20 mesh quartz particles above and below the catalyst bed. The steam and organic liquid entered into the top of the reactor which had an external electrical heater for temperature control and flowed downwardly through the catalyst bed. Both trans-stilbene and cis-stilbene, separated by chromatographic analysis and separately reported in the following experiments, react with ethylene by metathesis to form styrene. The minor biphenyl content, obtained from the chromatographic analysis, is also reported below.

EXAMPLE 1

The dehydrocoupled product containing by analysis 88.7 percent toluene, 1.8 percent benzene, 4.4 percent bibenzyl, 0.4 percent cis-stilbene, 3.4 percent trans-stilbene and 148 ppm. carbonyl was introduced into the reactor with an equal volume ratio of water. This purification treatment was carried out at a temperature of 550° C. and at atmospheric pressure. The gas stream was passed over a Girdler (Girdler Chemical Inc.) catalyst designated as G-64C (analyzing 58.0 percent $Fe_2O_3$, 23.0 percent $K_2CO_3$, 2.5 percent molybdenum oxide and less than 0.1 percent chromium oxide as its active portion) comprising 10–20 mesh particles at a liquid hourly space velocity of the organic components of 1.0 and a total LHSV of 2.0. After four hours of operation the effluent stream analyzed 88.6 percent toluene, 3.0 percent benzene, 0.9 percent bibenzyl and cis-stilbene (the chromatographic column did not separate these two components), 6.4 percent trans-stilbene and 47 ppm. carbonyl. After 34 hours of operation the product stream analyzed 89.0 percent toluene, 2.0 percent benzene, 2.1 percent bibenzyl and cis-stilbene, 5.6 percent trans-stilbene and 43 ppm. carbonyl. Following 63 hours of operation the effluent stream analyzed toluene 89.1 percent, benzene 2.0 percent, 2.2 percent bibenzyl and cis-stilbene, 5.4 percent trans-stilbene and 45 ppm. carbonyl.

EXAMPLE 2

In this experiment Girdler G-84 catalyst (comprising 88.0 percent $Fe_2O_3$, 10 percent $K_2CO_3$ and 2.0 percent $Cr_2O_3$) was utilized. The temperature was 500° C. and the other conditions of operation and the catalyst particle size were the same as in Example 1. The feed stream contained 86.9 percent toluene, 1.0 percent benzene, 0.1 percent biphenyl, 0.52 percent cis-stilbene, 6.1 percent bibenzyl and 4.0 percent trans-stilbene and analyzed 66 ppm. carbonyl. The product stream was analyzed every two hours. After operating for 10 hours the average analysis of the product stream was 89 percent toluene, 1.9 percent benzene, 0.19 percent biphenyl, 0.88 percent cis-stilbene, 0.57 percent bibenzyl, 6.86 percent trans-stilbene and 33 ppm. carbonyl.

EXAMPLE 3

The experiment of Example 2 was continued at an elevated temperature of 550° C. for 6 more hours. The product stream showed an average analysis at this temperature of operation of 87.2 percent toluene, 3.0 percent benzene, 0.23 percent biphenyl, 0.84 percent cis-stilbene, 0.26 percent bibenzyl, 7.80 percent trans-stilbene, and 36 ppm. carbonyl.

EXAMPLE 4

The experiment of Example 3 was continued at an elevated temperature of 600° C. for 6 more hours. The product stream showed an average analysis at this temperature of operation of 86.9 percent toluene, 5.82 percent benzene, 0.30 percent biphenyl, 0.72 percent cis-stilbene, 0.16 percent bibenzyl, 5.37 percent trans-stilbene, and 35 ppm. carbonyl.

EXAMPLE 5

The experiment of Example 2 was repeated using the same conditions including a temperature of 500° C. and same feed stream with a different catalyst. The catalyst was the Girdler G-64C catalyst which was modified to contain five percent zinc by impregnation with zinc nitrate solution followed by calcination. The product analysis after 10 hours of operation was 87.1 percent toluene, 1.17 percent benzene, 0.17 percent biphenyl, 0.73 percent cis-stilbene, 3.66 percent bibenzyl, 6.53 percent trans-stilbene and 21 ppm. carbonyl.

EXAMPLE 6

The experiment of Example 5 was continued at an elevated temperature of 550° C. After 6 hours of operation at this temperature, the product analyzed 86.4 percent toluene, 1.54 percent benzene, 0.21 percent biphenyl, 1.14 percent cis-stilbene, 0.41 percent bibenzyl, 9.53 percent trans-stilbene and 6 ppm. carbonyl.

EXAMPLE 7

The experiment of Example 6 was continued at 600° C. After 6 hours of operation with a product analysis every two hours, the average product analysis was 87.8 percent toluene, 2.50 percent benzene, 0.23 percent biphenyl, 0.99 percent cis-stilbene, 0.20 percent bibenzyl, 7.66 percent trans-stilbene and 25 ppm. carbonyl.

EXAMPLE 8

The experiment of Example 7 was continued at 650° C. After 6 hours of operation, the product analyzed 85.6 percent toluene, 5.97 percent benzene, 0.36 percent biphenyl, 0.96 percent cis-stilbene and bibenzyl combined, 5.97 percent trans-stilbene and 21 ppm. carbonyl.

EXAMPLE 9

The experiment of Example 2 was repeated using the same conditions, a temperature of 500° C. and the same feed but a different catalyst. The catalyst was a physical mixture of the Girdler G-64C catalyst and 50 wt. percent of a 6.15 percent ZnO on alumina catalyst. After 10 hours of operation, the product analysis was 87.5 percent toluene, 1.26 percent benzene, 0.25 percent biphenyl, 0.62 percent cis-stilbene, 4.15 percent bibenzyl, 5.73 trans-stilbene and 27 ppm. carbonyl.

EXAMPLE 10

Example 5 was repeated including a temperature of 500° C. with a different feed stream which analyzed 90.7 percent toluene, 0.97 percent benzene, 0.09 percent biphenyl, 0.44 percent cis-stilbene, 4.24 percent bibenzyl, 3.01 percent trans-stilbene and 69 ppm. carbonyl. Analysis of the purified product stream after five hours was 90.9 percent toluene, 0.90 percent benzene, 0.12 percent biphenyl, 0.54 percent cis-stilbene, 2.03 percent bibenzyl, 5.20 percent trans-stilbene and 22 ppm. carbonyl.

EXAMPLE 11

Example 10 was continued for one more hour at 500° C. and then the temperature in the purification reactor was elevated to 550° C. After operation at this elevated temperature for 2 hours, the product analysis showed 91.1 percent toluene, 1.55 percent benzene, 0.15 percent biphenyl, 0.66 percent cis-stilbene, 0.58 percent bibenzyl, 5.55 percent trans-stilbene and 17 ppm. carbonyl.

EXAMPLE 12

Crude oxidative dehydrocoupling effluent containing 50 percent steam on a volume basis was passed over a 10–20 mesh 19 percent chromia on alumina catalyst at a liquid hourly space velocity of 2.0, a temperature of 500° C. and at atmospheric pressure. This crude dehydrocoupling effluent analyzed 89.8 percent toluene, 0.71 percent benzene, 0.07 percent biphenyl, 0.41 percent cis-stilbene, 5.46 percent bibenzyl, 2.85 percent trans-stilbene and 74 ppm. carbonyl. After three hours of operation the product analyzed 90.8 percent toluene, 0.77 percent benzene, 0.10 percent biphenyl, 0.30 percent cis-stilbene, 4.66 percent bibenzyl, 3.05 percent trans-stilbene and 24 ppm. carbonyl.

EXAMPLE 13

The experiment of Example 12 was continued for 2 more hours and then the temperature was raised to 550° C. After two hours of operation at this temperature, the product analyzed 90.1 percent toluene, 1.21 percent benzene, 0.17 percent biphenyl, 0.42 percent cis-stilbene, 3.91 percent bibenzyl, 3.80 percent trans-stilbene and 26 ppm carbonyl.

EXAMPLE 14

The following runs demonstrated that the presence of carbon dioxide in the stream does not have an adverse effect on the removal of oxygen-containing impurities. The experiment of Example 5 was repeated except that the temperature was 550° C. and the dehydrocoupling product used as feed analyzed 90.7 percent toluene, 0.97 percent benzene, 4.24 percent bibenzyl, 0.44 percent cis-stilbene, 3.01 percent trans-stilbene, and 69 ppm. carbonyl. After 27.5 hours of operation the feed was changed to a dehydrocoupling product which contained by analysis 76.5 percent toluene, 2.04 percent benzene, 2.12 percent bibenzyl, 1.68 percent cis-stilbene, 15.7 percent trans-stilbene, and 96 ppm carbonyl. After 62 hours of operation with this feed, the product collected for the preceding two hours analyzed 75.8 percent toluene, 2.44 percent benzene, 0.73 percent bibenzyl, 2.06 percent cos-stilbene, 17.0 percent trans-stilbene, and 18 ppm carbonyl. The experiment was continued using the same conditions, except that 10 cc./min. $CO_2$ were introduced with the feed. After five hours of operation with $CO_2$, the product collected for the preceding two hours analyzed 77.5 percent toluene, 2.31 percent benzene, 1.48 percent bibenzyl, 1.82 percent cis-stilbene, 15.1 percent trans-stilbene, and 15 ppm. carbonyl.

EXAMPLE 15

The following two runs demonstrated the beneficial effect of removing carbonyl impurity from the crude dehydrocoupling product.

In this first experiment carbonyl impurity was not removed. After toluene was coupled over bismuth oxide, the great bulk of the water was removed, pure trans-stilbene was added to bring its content to about 10 percent and the remaining water was removed to less than five ppm. water in a molecular sieve. This product and ethylene in an ethylene to stilbene mol ratio of 8 to 1 were passed over an 8 percent tungsten on silica catalyst at a temperature of 480° C. and a pressure of 30 psig. The composition of the feed was 82.6 percent toluene, 0.88 percent benzene, 0.03 percent ethylbenzene, 0.08 percent styrene, 4.91 percent bibenzyl, 0.46 percent cis-stilbene, 10.3 percent trans-stilbene, and 0.78 percent other components including 96 ppm. carbonyl. After four hours of the ethenolysis reaction, the product stream analyzed 82.9 percent toluene, 0.94 percent benzene, 0.07 percent ethylbenzene, 0.39 percent styrene, 4.91 percent bibenzyl, 1.25 percent cis-stilbene, 8.51 percent trans-stilbene and 0.99 percent other components.

In the second experiment the carbonyl content of the feed stream was reduced from 66 ppm. to 15 ppm., the feed stream was dried and was then reacted under conditions identical with the preceding experiment. The feed to the reactor in this experiment was 83.3 percent toluene, 1.07 percent benzene, 4.67 percent bibenzyl, 0.22 percent cis-stilbene, 10.08 percent trans-stilbene and 0.67 percent other components. After four hours of ethenolysis the product stream analyzed 82.8 percent toluene, 1.07 percent benzene, 3.62 percent ethylbenzene, 6.33 percent styrene, 4.39 percent bibenzyl, 0.70 percent trans-stilbene and 1.09 percent other components. It is noted that the styrene content in these two experiments increased from 0.39 percent to 6.33 percent after carbonyl removal.

In the above detailed description our process is shown to substantially reduce the amount of oxygen-containing organic impurities from crude stilbene prepared by the oxidative dehydrocoupling of toluene. Derivatives of toluene can also be oxidatively dehydrocoupled using a solid oxidant to produce the corresponding stilbene derivatives. Examples of derivatives of toluene which can be oxidatively dehydrocoupled include ortho-, meta- and paraxylene; ortho-, meta- and parachlorotoluene; ortho-, meta- and paracyanotoluene; ortho-, meta- and paranitrotoluene; and the like. The oxygen-containing impurities can also be removed from these stilbene derivatives by the process of the present invention and these stilbene derivatives can then be converted to the corresponding styrene derivatives by metathesis with ethylene. Thus, for example, parachlorotoluene is dehydrocoupled to p,p'-dichlorostilbene, and this compound following removal of the oxygen-containing organic impurities is converted by ethenolysis to p-chlorostyrene.

It is to be understood that the above disclosure is by way of specific example and that numerous modifications and variations are available to those of ordinary skill in the art without departing from the true spirit and scope of the invention.

We claim:

1. The process for substantially increasing the amount of stilbene and substantially reducing the aromatic carbonyl and aromatic hydroxyl impurities in an organic composition comprising toluene, stilbene, benzene and bibenzyl and containing aromatic carbonyl and aromatic hydroxyl impurities which comprises contacting said organic composition with a catalyst comprising a Group VIb or Group VIII metal oxide, metal phosphate or a mixture thereof and a promoter amount of an alkali metal or an alkaline earth metal compound at a temperature between about 400° C. to about 700° C. in the presence of about two to about 90 weight percent steam, whereby the amount of stilbene is substantially increased and the amount of said aromatic carbonyl and aromatic hydroxyl impurities is substantially decreased.

2. The process for substantially increasing the amount of stilbene and substantially reducing the aromatic carbonyl and aromatic hydroxyl impurities in said organic composition in accordance with claim 1 in which the catalyst comprises at least about 45 weight percent of the Group VIb or Group VIII metal.

3. The process for substantially increasing the amount of stilbene and substantially reducing the aromatic carbonyl and aromatic hydroxyl impurities in said organic composition in accordance with claim 1 in which the alkali metal is potassium present in an amount between about 0.5 and about 50 weight percent determined as potassium oxide.

4. The process for substantially increasing the amount of stilbene and substantially reducing the aromatic carbonyl and aromatic hydroxyl impurities in said organic composition in accordance with claim 1 in which the catalyst comprises up to about 15 percent zinc in the form of zinc oxide.

5. The process for substantially increasing the amount of stilbene and substantially reducing the aromatic carbonyl and aromatic hydroxyl impurities in said organic composition in accordance with claim 4 in which the zinc is deposited onto said Group VIb or Group VIII metal oxide or metal phosphate.

6. The process for substantially increasing the amount of stilbene and substantially reducing the aromatic carbonyl and aromatic hydroxyl impurities in said organic composition in accordance with claim 4 in which the zinc is deposited on a support and is admixed with said Group VIb or Group VIII metal oxide or metal phosphate in a heterogeneous mixture.

7. The process for substantially increasing the amount of stilbene and substantially reducing the aromatic carbonyl and aromatic hydroxyl impurities in said organic composition in accordance with claim 1 in the presence of about 10 to about 75 weight percent steam.

8. The process for substantially increasing the amount of stilbene and substantially reducing the aromatic carbonyl and aromatic hydroxyl impurities in said organic composition in accordance with claim 1 in which the catalyst is supported on an inert support.

9. The process for substantially increasing the amount of stilbene and substantially reducing the aromatic carbonyl and aromatic hydroxyl impurities in said organic composition in accordance with claim 1 in which the carbonyl content of the said organic composition is reduced to a maximum of about 50 parts per million.

10. The process for substantially increasing the amount of stilbene and substantially reducing the aromatic carbonyl and aromatic hydroxyl impurities in said organic composition in accordance with claim 1 in which the carbonyl content of the said organic composition is reduced to a maximum of about 35 parts per million.

11. The process for substantially increasing the amount of stilbene and substantially reducing the aromatic carbonyl and aromatic hydroxyl impurities in said organic composition in accordance with claim 1 in which the carbonyl content of the said organic composition is reduced to a maximum of about 20 parts per million.

12. The process for substantially increasing the amount of stilbene and substantially reducing the aromatic carbonyl and aromatic hydroxyl impurities in said organic composition in accordance with claim 1 in which the amount of benzene is substantially increased.

13. The process for substantially increasing the amount of stilbene and substantially reducing the aromatic carbonyl and aromatic hydroxyl impurities in said organic composition in accordance with claim 1 in which the amount of bibenzyl is substantially reduced.

14. The process for producing styrene from ethylene and toluene which comprises
    (a) dehydrocoupling toluene in the presence of a solid oxide oxidant at a temperature of between about 500° and about 700° C. to form a gaseous product stream comprising toluene, benzene, bibenzyl, stilbene, a minute amount of oxygen-containing aromatic impurities, carbon dioxide and about two to about 90 weight percent water,
    (b) contacting said gaseous product stream at a temperature between about 400° and about 700° C. with a first catalyst comprising a Group VIb or a Group VIII metal oxide, metal phosphate or a mixture thereof and a promoter amount of an alkali metal or alkaline earth metal compound to substantially increase the amount of stilbene and substantially reduce the amount of oxygen-containing aromatic impurities,
    (c) removing a substantial amount of water from the purified product stream, and
    (d) contacting the substantially water-free reaction product with ethylene in the presence of a disproportionation catalyst at a temperature between about 150° and about 650° C. whereby stilbene and ethylene react to form styrene, and
    (e) separating styrene from the reaction product.

15. The process for producing styrene from ethylene and toluene in accordance with claim 14 in which the said first catalyst comprises up to about 15 present zinc as zinc oxide.

16. The process for producing styrene from ethylene and toluene in accordance with claim 14 in which the said gaseous product stream comprises about 10 to about 75 weight percent steam.

17. The process for producing styrene from ethylene and toluene in accordance with claim 15 in which the said first catalyst comprises at least about 45 percent iron and between about 0.5 and about 50 percent potassium as potassium oxide.

18. The process for producing styrene from ethylene and toluene in accordance with claim 14 in which the said gaseous product stream is purified without substantial cooling of said gaseous product stream.

19. The process for producing styrene from ethylene and toluene in accordance with claim 14 in which the carbonyl content of the purified product stream is a maximum of about 50 ppm.

20. The process for producing styrene from ethylene and toluene in accordance with claim 14 in which the water is removed from the purified product stream to a maximum of about 20 ppm.

21. The process for producing styrene from ethylene and toluene in accordance with claim 14 in which the carbon dioxide is substantially removed from the purified product stream.

22. The process for producing styrene from ethylene and toluene in accordance with claim 19 in which the carbonyl content of the purified product stream is a maximum of about 35 ppm.

23. The process for producing styrene from ethylene and toluene in accordance with claim 22 in which the carbonyl content of the purified product stream is a maximum of about 20 ppm.

* * * * *